(12) United States Patent
Kitzman et al.

(10) Patent No.: US 8,383,338 B2
(45) Date of Patent: Feb. 26, 2013

(54) METHODS AND SYSTEMS FOR UNIFORM ENRICHMENT OF GENOMIC REGIONS

(75) Inventors: Jacob Kitzman, Madison, WI (US);
Todd Richmond, Madison, WI (US);
Mark D'Ascenzo, Monona, WI (US);
Thomas Albert, Fitchburg, WI (US);
Matthew Rodesch, Stoughton, WI (US);
Jeffrey Jeddeloh, Verona, WI (US);
Christina Middle, Madison, WI (US)

(73) Assignee: Roche NimbleGen, Inc., Madison, WI (US)

( * ) Notice: Subject to any disclaimer, the term of this patent is extended or adjusted under 35 U.S.C. 154(b) by 364 days.

(21) Appl. No.: 12/391,001

(22) Filed: Feb. 23, 2009

(65) Prior Publication Data

US 2009/0221438 A1    Sep. 3, 2009

Related U.S. Application Data

(63) Continuation-in-part of application No. 11/970,949, filed on Jan. 8, 2008, now abandoned, which is a continuation of application No. 11/789,135, filed on Apr. 24, 2007, now abandoned.

(60) Provisional application No. 61/032,594, filed on Feb. 29, 2008, provisional application No. 60/832,719, filed on Jul. 21, 2006, provisional application No. 60/794,560, filed on Apr. 24, 2006.

(51) Int. Cl.
*C12Q 1/68* (2006.01)
*C12P 19/34* (2006.01)
*C07H 21/00* (2006.01)

(52) U.S. Cl. ....... 435/6.1; 435/91.2; 536/22.1; 536/25.4

(58) Field of Classification Search ..... 435/6; 536/23.1, 536/24.3
See application file for complete search history.

(56) References Cited

U.S. PATENT DOCUMENTS

| | | | |
|---|---|---|---|
| 5,432,065 A | 7/1995 | Fuller | |
| 5,605,662 A | 2/1997 | Heller et al. | |
| 5,804,384 A | 9/1998 | Muller et al. | |
| 5,837,832 A | 11/1998 | Chee et al. | |
| 5,846,717 A | 12/1998 | Brow et al. | |
| 5,874,215 A * | 2/1999 | Kuiper et al. | 435/6 |
| 6,013,440 A | 1/2000 | Lipshutz et al. | |
| 6,287,765 B1 | 9/2001 | Cubicciotti | |
| 6,638,722 B2 * | 10/2003 | Ji et al. | 435/6 |
| 7,202,039 B2 | 4/2007 | Su | |
| 7,452,671 B2 | 11/2008 | Shapero et al. | |
| 7,851,158 B2 * | 12/2010 | McKernan | 435/6.11 |
| 7,901,886 B2 | 3/2011 | Staehler et al. | |
| 2003/0232348 A1 | 12/2003 | Jones et al. | |
| 2004/0110166 A1 | 6/2004 | Macevicz | |
| 2004/0121364 A1 | 6/2004 | Chee et al. | |
| 2004/0142324 A1 * | 7/2004 | Bosio | 435/6 |
| 2005/0009020 A1 | 1/2005 | Distler | |
| 2005/0040043 A1 | 2/2005 | Stahler et al. | |
| 2005/0142577 A1 | 6/2005 | Jones et al. | |
| 2005/0176019 A1 | 8/2005 | Beutel et al. | |
| 2005/0282209 A1 | 12/2005 | Albert et al. | |
| 2006/0240424 A1 | 10/2006 | Inbe et al. | |
| 2008/0125324 A1 * | 5/2008 | Petersdorf et al. | 506/1 |
| 2008/0254472 A1 | 10/2008 | Inui | |
| 2009/0081737 A1 | 3/2009 | Brenner | |

FOREIGN PATENT DOCUMENTS

| | | |
|---|---|---|
| EP | 1143252 A | 10/2001 |
| EP | 1 184 466 A2 | 3/2002 |
| GB | 2436976 A | 10/2007 |
| WO | 0079006 A1 | 12/2000 |
| WO | 03031965 A3 | 4/2003 |
| WO | 2005010199 A2 | 2/2005 |
| WO | 2005/042763 A | 5/2005 |
| WO | 2007/057652 A1 | 5/2007 |
| WO | 2008045251 A2 | 4/2008 |
| WO | 2008/115185 A | 9/2008 |

OTHER PUBLICATIONS

Saiki et al. Genetic analysis of amplified DNA with immobilized sequence-specific oligonucleotide probes PNAS 86(16) : 6230-6234 (1989).*
Sanger et al., DNA sequencing with chain-terminating inhibitors. PNAS 74 : 5463-5467 (1977).*
Gene Characterization Kits ; The Stratagene Catalog p. 39 (1988).*
International Search Report dated Oct. 29, 2008 (International Patent Application No. PCT/US2007/01064; filed Apr. 24, 2007).
International Search Report dated May 15, 2009 (International Patent Application No. PCT/EP2009/001307; filed Sep. 3, 2009).
Broude, Natalie E. et al. "DNA microarrays with stem-loop DNA probes: preparation and applications", Nucleic Acids Research, 2001, pp. 1-11, vol. 29—No. 9, Oxford University Press, USA.
Han, Eugene S. et al., "RecJ exocuclease:substrates, products and interaction withn SSB," Nucleic Acids Research, Feb. 18, 2006, pp. 1084-1091, vol. 34—No. 4, Oxford University Press, USA.
Fors, Lance et al., "Large-scale SNP scoring from unamplified genomic DNA", Pharmacogenomics, 2000, pp. 219-229, vol. 1—No. 2, Ashley Publications Ltd., USA.
International Search Report dated Jul. 2, 2009 (International Patent Application No. PCT EP2009/002318; filed Jul. 2, 2009).
Calhoun, Identifying Allelic Loss and Homozygous Deletions in Pancreatic Cancer without Matched Normals Using High-Density Single-Nucleotide Polymorphism Arrays, Cancer Res 2006; 66: (16). Aug. 15, 2006.

(Continued)

Primary Examiner — Ethan C Whisenant
(74) Attorney, Agent, or Firm — Quarles & Brady LLP

(57) ABSTRACT

The present invention provides methods and compositions for the enrichment of target nucleic acids in a microarray system. In particular, the present invention provides methods and compositions for uniform enrichment of target nucleic acid molecules in a microarray format. The present invention also provides for intentionally non-uniform enrichment among target nucleic acid molecules.

27 Claims, 8 Drawing Sheets

OTHER PUBLICATIONS

Garraway et al., Array-based approaches to cancer genome analysis, Drug Discovery Today: Disease Mechanisms, Elsevier Ltd, vol. 2, No. 2, 2005.

Wilkins Stevens, et al. "Analysis of single nucleotide polymorphisms with solid phase invasive cleavage reactions" Nucleic Acids Research, Oxford University Press, vol. 29, No. 16, 2001.

Hodges, Emily et al: Genome-wide in situ exon capture for selective resequencing. Nature Genetics, Dec. 2007, pp. 1522-1527; vol. 39, No. 12.

Okou, David T. et al: Microarray-based genomic selection for high-throughput resequencing. Nature Methods, Nov. 2007, pp. 907-909; vol. 4, No. 11.

Davis et al., Section 5-5-5.6. Basic Methods in Molecular Biology. pp. 42-43, Elsevier Science Publishing. New York, New York (1986).

Albert, Thomas J. et al., "Direct selection of human genomic loci by microarray hybridization," Nature Methods, vol. 4, No. 11, pp. 903-905 (2007).

International Preliminary Report on Patentability dated Apr. 15, 2010 (PCT/EP2009/001307 filed Feb. 24, 2009).

Examination Report dated Feb. 3, 2011; European Patent Application No. 09 714 916.5.

Applicant's Reply to International Preliminary Report on Patentability (PCT/EP2009/001307 filed Feb. 24, 2009); Reply filed Oct. 29, 2010.

* cited by examiner

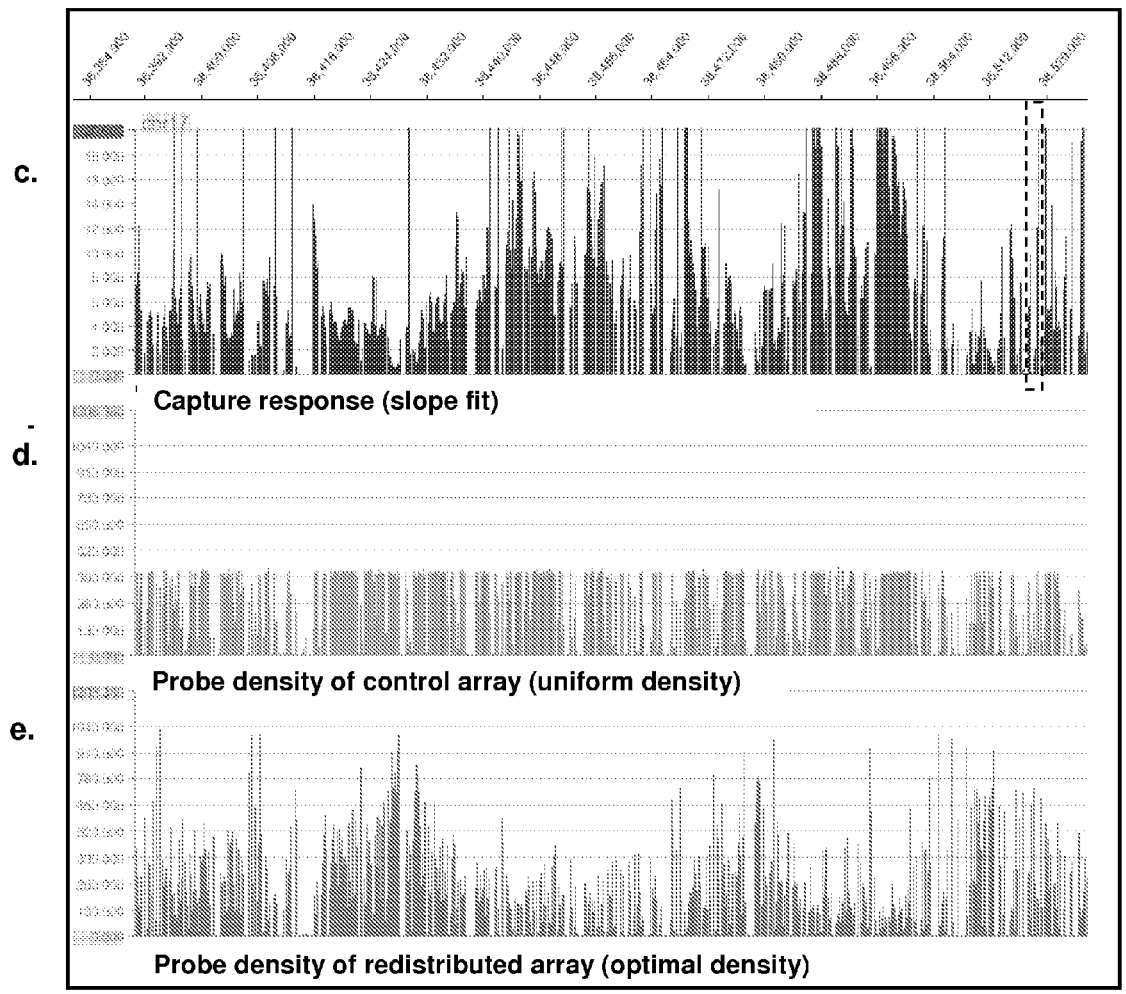
FIG. 1C-E a)

b)

METHODS AND SYSTEMS FOR UNIFORM ENRICHMENT OF GENOMIC REGIONS

The present invention claims priority to U.S. provisional patent application Ser. No. 61/032,594 filed on Feb. 29, 2008, and to U.S. continuation-in-part patent application Ser. No. 11/970,949 filed Jan. 8, 2008 which claims priority to U.S. patent application Ser. No. 11/789,135 filed Apr. 24, 2007 which claims priority to U.S. provisional patent application Ser. Nos. 60/832,719 filed Jun. 21, 2006 and 60/794,560 filed Apr. 24, 2006. Each application is incorporated herein by reference in its entirety.

FIELD OF THE INVENTION

The present invention provides methods and compositions for the enrichment of target nucleic acids in a microarray system. In particular, the present invention provides methods and compositions for uniform enrichment of target nucleic acid molecules in a microarray format. The present invention also provides for intentionally non-uniform enrichment among target nucleic acid molecules.

BACKGROUND OF THE INVENTION

The advent of nucleic acid microarray technology makes it possible to build an array of millions of nucleic acid sequences in a very small area, for example on a microscope slide (e.g., U.S. Pat. Nos. 6,375,903 and 5,143,854). Initially, such arrays were created by spotting pre-synthesized DNA sequences onto slides. However, the construction of maskless array synthesizers (MAS) as described in U.S. Pat. No. 6,375,903 now allows for the in situ synthesis of oligonucleotide sequences directly on the slide itself.

Using a MAS instrument, the selection of oligonucleotide sequences to be constructed on the microarray is under software control such that it is now possible to create individually customized arrays based on the particular needs of an investigator. In general, MAS-based oligonucleotide microarray synthesis technology allows for the parallel synthesis of over 4 million unique oligonucleotide features in a very small area of a standard microscope slide. With the availability of the entire genomes of hundreds of organisms, for which a reference sequence has generally been deposited into a public database, microarrays have been used to perform sequence analysis on nucleic acids isolated from a myriad of organisms.

Nucleic acid microarray technology has been applied to many areas of research and diagnostics, such as gene expression and discovery, mutation detection, allelic and evolutionary sequence comparison, genome mapping, drug discovery, and more. Many applications require searching for genetic variants and mutations across the entire human genome; variants and mutations that, for example, may underlie human diseases. In the case of complex diseases, these searches generally result in a single nucleotide polymorphism (SNP) or set of SNPs associated with one or more diseases. Identifying such SNPs has proven to be an arduous, time consuming, and costly task wherein resequencing large regions of genomic DNA, usually greater than 100 kilobases (Kb) from affected individuals and/or tissue samples is frequently required to find a single base change or identify all sequence variants.

The genome is typically too complex to be studied as a whole, and techniques must be used to reduce the complexity of the genome. To address this problem, one solution is to reduce certain types of abundant sequences from a DNA sample, as found in U.S. Pat. No. 6,013,440. Alternatives employ methods and compositions for enriching genomic sequences as described, for example, in Albert et al. (2007, Nat. Meth., 4:903-5, Epub 2007 Oct. 14) and Okou et al. (2007, Nat. Meth. 4:907-9, Epub 2007 Oct. 14). Albert et al. disclose an alternative that is both cost-effective and rapid in effectively reducing the complexity of a genomic sample in a user defined way to allow for further processing and analysis.

However, it is equally important to be able to enrich target sequences uniformly over the targeted region(s). If enrichment is not uniform, for example, some target sequences will be captured disproportionately compared to other target sequences thereby negating downstream applications that are dependent on approximately uniform distribution of targeted sequences. Hodges et al. (2007, Nat. Meth. 39:1522-1527, Epub 2007 Nov. 4) noted that a critical parameter in microarray capture was the introduction of biased target capture which greatly affects sequence coverage depth. However, Hodges offered no path forward, other than to say that probe redistribution to compensate for biased capture would necessarily introduce other types of biases that would lead to problems with downstream applications, for example sequencing applications.

As such, what are needed are methods and compositions to provide uniform capture, and hence representation, of captured targets during capture and enrichment of targeted sequences in a microarray format. Conversely, an investigator might also require a conscience non-uniformity of capture, for example if an investigator envisions targeting exons over intergenic regions. Such methods would provide maximum data utility to investigators in their endeavors to understand and identify, for example, causes of disease and associated therapeutic treatments.

SUMMARY OF THE INVENTION

The present invention provides methods and compositions for the enrichment of target nucleic acids in a microarray system. In particular, the present invention provides methods and compositions for uniform enrichment of target nucleic acid molecules in a microarray format. The present invention also provides for intentionally non-uniform enrichment among target nucleic acid molecules.

Nucleic acid enrichment reduces the complexity of a large nucleic acid sample, such as a genomic DNA sample, cDNA library or mRNA library, to facilitate further processing and genetic analysis. Pre-existing nucleic acid capture methods utilize immobilized nucleic acid probes to capture target nucleic acid sequences (e.g. as found in genomic DNA, cDNA, mRNA, etc.) by hybridizing the sample to probes immobilized on a solid support. The captured target nucleic acids, as found for example in genomic DNA, are washed and eluted off of the solid support-immobilized probes. The eluted genomic sequences are more amenable to detailed genetic analysis than a genomic sample that has not been subjected to this procedure. Enrichment of target nucleic acid sequences takes nucleic acid capture one step further, by reducing the complexity of a sample wherein sequences of interest are selected for, or enriched, by selective processes. Enrichment methods and compositions are fully disclosed in U.S. patent application Ser. Nos. 11/789,135 and 11/970,949 and World Intellectual Property Organization Application Number PCT/US07/010,064, all of which of incorporated herein by reference in their entireties.

Enrichment of target nucleic acids in a microarray format is important in reducing the complexity of a nucleic acid sample prior to, for example, sequencing or other downstream applications. However, many downstream applications strongly depend upon the resulting sequencing reads having an approximately uniform distribution over the target regions, as disproportionately high representation of some targets necessarily depletes others. Although array-based enrichment robustly enriches targeted fragments, it is contemplated that certain targets are more strongly enriched than others thereby producing biased capture or targets.

As such, the present invention provides methods and compositions to address this biased target nucleic acid capture. For example, embodiments of the present invention provide for array design that is modified to redistribute probes from targets with above-average enrichment to those with below-average enrichment. In developing embodiments of the present invention, it was determined that this redistribution of probes significantly improves the uniformity of enrichment among captured targets. Conversely, the present invention also provides for array design that is modified to redistribute probes that intentionally introduce biased target capture into an array. For example, if an investigator is interested in capturing specific genomic regions over other genomic regions, the methods as described herein can be utilized to create captured bias.

Certain illustrative embodiments of the invention are described below. The present invention is not limited to these embodiments.

In some embodiments, the present invention comprises a solid support microarray, generally comprising support-immobilized nucleic acid probes to capture and enrich for specific nucleic acid sequences (target nucleic acids) from a sample (e.g., genomic DNA, cDNA, mRNA, tRNA, etc.). In some embodiments, the probes that are immobilized on a support represent a redistributed set of probes. For example, the redistributed probes are designed to provide uniform capture of target regions, such that capture of targets is not biased. In some embodiments, the probes that are immobilized on a support are redistributed probes, wherein said probes are designed to provide non-uniform capture of target regions, such that capture of targets is intentionally biased.

In some embodiments, target nucleic acid enrichment is via hybridizing a nucleic acid sample, for example a genomic DNA sample, which may contain one or more target nucleic acid sequence(s), against a microarray comprising redistributed nucleic acid probes directed to a specific region or specific regions of the genome. After hybridization, target nucleic acid sequences present in the sample are enriched by washing the array and eluting the hybridized genomic nucleic acids from the array. Following elution, the enriched samples are assayed for the level or amount of enrichment over a control. In some embodiments, the target nucleic acid sequence(s) are further amplified using, for example, non-specific ligation-mediated PCR (LM-PCR), resulting in an amplified pool of PCR products of reduced complexity compared to the original sample for sequencing, library construction, and other applications. In some embodiments, the assay comprising redistributed probes for capture of target sequences demonstrates a uniform, unbiased capture over the target region as exemplified in FIG. 1.

In some embodiments, the present invention comprises a solid support, generally comprising support-immobilized nucleic acid probes to capture specific nucleic acid sequences (target nucleic acids) from a sample (e.g., genomic DNA, cDNA, mRNA, tRNA, etc.). In some embodiments, the solid support is a slide, for example a microarray slide. In some embodiments, the solid support comprises beads, whereas the beads are in solution, for example in a tube or other such container, or for example aliquoted into wells of an assay plate (e.g., 12 well, 24 well, 96 well, 384 well, and the like). In some embodiments, the probes that are immobilized on a support represent a redistributed set of probes. For example, the redistributed probes are designed to provide uniform capture of target nucleic acid molecule regions, such that capture of targets is not biased, and such that the frequency of each individual sequence of the immobilized probes corresponds to the frequency of the corresponding target nucleic acid sequence within the population of the target nucleic acid molecules. In some embodiments, the probes that are immobilized on a support are redistributed probes, wherein said probes are designed to provide non-uniform capture of target regions, such that capture of targets is intentionally biased. In some embodiments, the sample is fragmented, for example by sonication, or other methods capable of fragmenting nucleic acids. In some embodiments, the fragmented sample (e.g., fragmented genomic DNA, cDNA, etc.) is modified by ligation to linkers on one or both of the 5' and 3' ends. In some embodiments, the 5' and 3' ends of a fragmented sample are first prepared for ligation with a linker, for example by performing a "fill in" reaction with Klenow enzyme.

The preparation of nucleic acid ends for subsequent ligation to linkers is well known in the art, and can be found in any molecular cloning manual such as "Molecular Cloning: A Laboratory Manual, Sambrook et al. Eds, Cold Spring Harbor Laboratory Press", which is herein incorporated be reference in its entirety. Indeed, exemplary methods for performing all molecular cloning, hybridization, washing, and elution techniques as used herein can be found in "Molecular Cloning: A Laboratory Manual", Sambrook et al., Eds, Cold Spring Harbor Press as well as "A Molecular Cloning Manual: DNA Microarrays", Bowtell et al., Eds, Cold Spring Harbor Press (incorporated herein by reference in their entireties) as well as other technical manuals and reference guides known to skilled artisans. In some embodiments, the fragmented and linker-adapted nucleic acid sample is hybridized to an array comprising redistributed probes designed to capture target sequences in an unbiased manner, and the targeted sequences are captured. In other embodiments, the fragmented and linker-adapted nucleic acid sample is hybridized to an array comprising redistributed probes designed to intentionally capture target sequences in a biased manner, and the target sequences are captured. The use of linkers for enrichment methods and enrichment methods in general are well known and fully described in U.S. patent application Ser. Nos. 11/789,135 and 11/970,949 and World Intellectual Property Organization Application Number PCT/US07/010,064, and further in Albert et al. (2007), Okou et al. (2007) and Hodges et al. (2007); all of which of incorporated herein by reference in their entireties.

Following hybridization, non-targeted nucleic acids are washed from the microarray and the bound, targeted nucleic acids are eluted from the array following protocols known in the art. The quality of the enriched sample is calculated and fold enrichment is determined and communicated to the user. In some embodiments, the calculation of enrichment comprises fold enrichment as compared to a control enrichment sample. Samples of sufficient quality are used for downstream applications, such as sequencing, cloning, library construction, etc.

The present invention is not limited by any downstream use of enriched nucleic acids, and a skilled artisan will understand the myriad uses such a sample would provide including, but not limited to, sequencing, SNP detection for discovery and correlation with disease states and risk factors, use of targeted sequences in drug discovery applications, etc.

Enriched target sequences can be assessed for, for example, the quality of microarray based enriched target nucleic acids (e.g., level of effectiveness of the unbiased (or intentionally biased) enrichment methods as described herein). Such assessment not only provides insight into the general effectiveness of the enrichment technology, but it also provides an investigator a method of accessing the quality of the enriched nucleic acids prior to spending precious time and resources on downstream applications with a sample that is not appropriately enriched. In some embodiments, the assessing of the quality of the target nucleic acids is performed by testing the enrichment of a subset of reference sequences, for example conserved regions in a genome, as found in U.S. Patent Provisional Application 61/026,596, incorporated herein by reference in its entirety.

In one embodiment, the present invention comprises a method for uniform enrichment of a population of nucleic acid molecules in a sample, comprising providing a sample of nucleic acid molecules comprising a plurality of target nucleic acid sequences, hybridizing the sample to a support comprising immobilized nucleic acid probes under conditions to support hybridization between the immobilized nucleic acid probes and the plurality of target nucleic acid sequences, wherein said immobilized nucleic acid probes are complementary to said plurality of target nucleic acid sequences, and wherein said immobilized nucleic acid probes provide uniform hybridization among said plurality of target nucleic acid sequences, and separating non-hybridized nucleic acid sequences from hybridized target nucleic acid sequences thereby enriching a population of nucleic acid molecules in a sample. In some embodiments, separating the hybridized and non-hybridized sequences comprises washing the support such that non-hybridized nucleic acid sequences are removed from the support. In some embodiments, the nucleic acid molecules are fragmented prior to hybridization and in further embodiments the fragments are ligated to adaptor molecules at one or both ends. In some embodiments, the linker adapted fragmented nucleic acid molecules are denatured prior to hybridization. In some embodiments, the hybridized target nucleic acid sequences are eluted from the support and oftentimes sequenced after elution. In some embodiments, the support is a solid support, wherein said solid support is a microarray slide or a bead. In preferred embodiments, the nucleic acid molecules are genomic DNA molecules or amplified genomic DNA molecules. In preferred embodiments, the nucleic acid probes are characterized in that the frequency of the individual sequences of the immobilized nucleic acid probes corresponds to the frequency of the corresponding plurality of target nucleic acid sequences within a population of nucleic acid molecules, wherein determining the frequency comprises utilizing an empirically-fit linear regression model.

In one embodiment, the present invention comprises a solid support and a plurality of nucleic acid probes immobilized on said solid support, wherein each of said plurality of immobilized nucleic acid probes provides for uniform hybridization among a plurality of target nucleic acid sequences.

In one embodiment, the present invention provides a kit for performing uniform enrichment of target nucleic acid sequences comprising one or more containers, wherein said one or more containers comprises a solid support comprising immobilized nucleic acid probes, wherein said probes are selected from a group consisting of a plurality of probes hybridizable to a plurality of target nucleic acid sequences and wherein said probes provide for uniform enrichment of said plurality of target nucleic acid sequences, and one or more reagents for performing hybridizations, washes, and elution of target nucleic acid sequences.

In one embodiment, the present invention provides a process for uniform enrichment of a population of nucleic acid sequences in a sample comprising a plurality of immobilized hybridization probe sequences wherein the frequency of the individual sequences of the immobilized hybridization probes corresponds to the frequency of a plurality of corresponding target nucleic acid sequences within a population of nucleic acid molecules, and wherein said process for uniform enrichment comprises hybridizing said probes to corresponding target nucleic acid sequences and separating non-hybridized nucleic acid sequences from hybridized target nucleic acid sequences. In some embodiments, the process further comprises eluting the hybridized target nucleic acid sequences. In preferred embodiments, the hybridization of probe and target sequences within the process is performed on a solid support such as a microarray slide or bead. In preferred embodiments, determining the frequency of probe sequences comprises utilizing an empirically-fit linear regression model. In some embodiments, the sample used in the process is a genomic DNA sample.

DEFINITIONS

As used herein, the term "sample" is used in its broadest sense. In one sense, it is meant to include a nucleic acid specimen obtained from any source. Biological nucleic acid samples may be obtained from animals (including humans) and encompass nucleic acids isolated from fluids, solids, tissues, etc. Biological nucleic acid sample may also come from non-human animals, including, but are not limited to, vertebrates such as rodents, non-human primates, ovines, bovines, ruminants, lagomorphs, porcines, caprines, equines, canines, felines, aves, etc. Biological nucleic acids may also be obtained from prokaryotes, like bacteria and other non-animal eukaryotes such as plants. It is contemplated that the present invention is not limited by the source of nucleic acids sample, and any nucleic acid from any biological Kingdom finds utility in methods as described herein.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The term oligonucleotide may also be used interchangeably with the term "polynucleotide."

As used herein, the terms "complementary" or "complementarity" are used in reference to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on, for example, the efficiency and strength of hybridization between nucleic acid strands, amplification specificity, etc.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. While the invention is not limited to a particular set of hybridization conditions, stringent hybridization conditions are preferably employed. Stringent hybridization conditions are sequence-dependent and will differ with varying environmental parameters (e.g., salt concentrations, and presence of organics). Generally, "stringent" conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

By way of example, "stringent conditions" or "high stringency conditions," comprise hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C., with washes at 42° C. in 0.2×SSC (sodium chloride/sodium citrate) and 50% formamide at 55° C., followed by a wash with 0.1×SSC containing EDTA at 55° C. For moderately stringent conditions, it is contemplated that buffers containing 35% formamide, 5×SSC, and 0.1% (w/v) sodium dodecyl sulfate are suitable for hybridizing at 45° C. for 16-72 hours. Furthermore, it is contemplated that formamide concentration may be suitably adjusted between a range of 20-45% depending on the probe length and the level of stringency desired. In some embodiments of the present invention, probe optimization is obtained for longer probes (for example, greater than 50 mers) by increasing the hybridization temperature or the formamide concentration to compensate for a change in the probe length. Additional examples of hybridization conditions are provided in many reference manuals, for example in "Molecular Cloning: A Laboratory Manual", as referenced and incorporated herein.

Similarly, "stringent" wash conditions are ordinarily determined empirically for hybridization of target sequences to a corresponding probe array. For example, the arrays are first hybridized and then washed with wash buffers containing successively lower concentrations of salts, or higher concentrations of detergents, or at increasing temperatures until the signal-to-noise ratio for specific to non-specific hybridization is high enough to facilitate detection of specific hybridization. By way of example, stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 150 mM. Stringent wash and hybridization conditions are known to those skilled in the art, and can be found in, for example, Wetmur et al., 1966, J Mol Biol 31:349-70 and Wetmur, 1991, Crit. Rev Bio Mol Biol 26:227-59; incorporated herein by reference in their entireties.

It is well known in the art that numerous equivalent conditions may be employed to adjust and regulate stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered. As such, the components and concentrations of hybridization and wash solutions will vary to generate conditions of stringency. In preferred embodiments of the present invention, hybridization and wash solutions are utilized as found commercially available through Roche-NimbleGen (e.g., NimbleChip™ CGH Arrays, NimbleGen Hybridization Kits, etc.).

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. With PCR, it is possible to amplify a single copy of a specific target sequence in genomic DNA to a level detectable by several different methodologies known to those skilled in the art. In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. Ligation mediated PCR refers to PCR that is performed, wherein the primers are homologous (e.g., complementary) to linkers that are ligated to the ends of DNA (e.g., DNA fragments).

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded, however in the present invention the probes are intended to be single stranded. Probes are useful in the detection, identification and isolation of particular gene sequences As used herein, the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "purified" or "to purify" refers to the removal of components (e.g., contaminants) and/or contaminants from a sample. The term "purified" refers to molecules, either nucleic or amino acid sequences that are removed from their natural environment, isolated or separated. An "isolated nucleic acid sequence or sample" is therefore a purified nucleic acid sequence or sample. "Substantially purified" molecules are at least 60% free, preferably at least 75% free, and more preferably at least 90% free from other components with which they are naturally associated.

DETAILED DESCRIPTION OF THE INVENTION

Figure 1A:
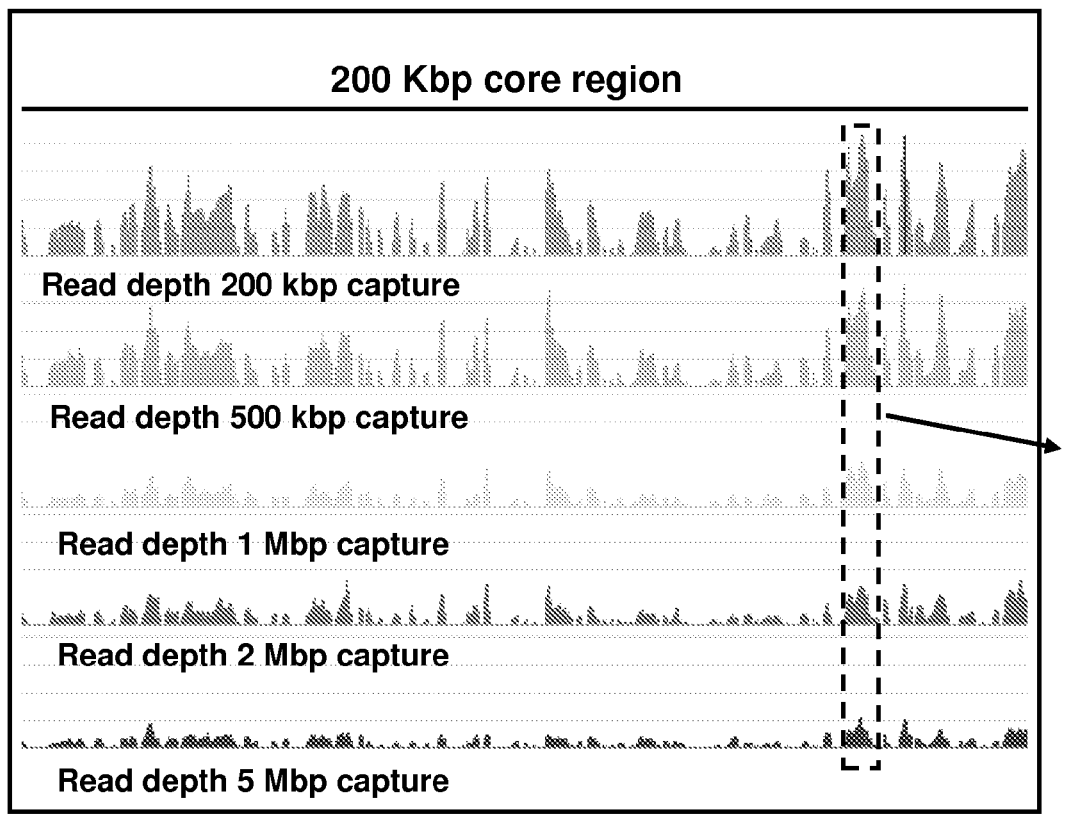
FIG. 1 demonstrates exemplary probe redistribution data using empirical optimization to mitigate locally-biased target capture: a) read depths along the core 200 kbp region of nested target intervals in five separate capture experiments demonstrate larger target regions correlate with lower sequencing depth; b) capture response calculated within one localized window by fitting windowed read depth to capture probe density across the capture experiments; c) capture response along the targeted region demonstrates areas of bias with excessive or insufficient capture; d) a control array demonstrates probes uniformly distributed along the target; e) whereas in the optimized array probes are redistributed non-uniformly so as to achieve a uniform distribution of reads following capture and sequencing.

Targeted genomic sequencing is one of the most important biomedical applications of next-generation sequencing technologies. A revolutionary way to target next generation sequencing utilizes oligonucleotide microarrays as sample preparation devices. These arrays capture regions of the genome defined by the array probes, which are then eluted and, for example, sequenced. Because of the relatively high per run cost of next generation sequencing, it is important to have robust quality control metrics that ensure that only samples that are highly enriched for target regions are sequenced. Two important characteristics of successfully captured samples are 1) highly enriched for targeted regions, and 2) uniformly enriched across all targeted regions. The present invention provides assays that demonstrate uniform enrichment across target areas of a genome.

Sequence capture in a microarray format facilitates selective enrichment of nucleic acids prior to downstream applications, for example sequencing. When performing selective enrichment, a nucleic acid sample, for example a DNA or RNA sample, is hybridized to a microarray comprised of oligonucleotide probes complementary to desired target sequences. The targeted, captured nucleic acids are eluted from the array, with the resulting fraction being enriched by several orders of magnitude for targeted fragments when compared to a control array. Enrichment methods are more completely described in U.S. patent application Ser. Nos. 11/789,135 and 11/970,949 and World Intellectual Property Organization Application Number PCT/US07/010,064, and further in Albert et al. (2007), Okou et al. (2007) and Hodges et al. (2007); all of which of incorporated herein by reference in their entireties.

Many downstream applications strongly depend upon, for example, an approximately uniform distribution of capture over the target capture region, as it is contemplated that disproportionately high representation of some targets deplete other targets. In developing embodiments of the present invention, novel methods were developed to deal with this biased, disproportionate target capture, wherein probes are redistribution from targets demonstrating above average enrichment to probes demonstrating below average enrichment. As demonstrated herein, the probe redistribution methods of the present method significantly improve the uniformity of enrichment among captured targets.

The present invention provides methods for determining and designing microarrays comprising redistributed oligonucleotide probes to allow for uniform, or intentionally non-uniform, capture of target nucleic acid molecules. In developing embodiments of the present invention, capture and sequencing microarray experiments were performed using a nested set of target regions centered on human chromosome 17q21.31. As an indirect measure of target sequence relative abundance following capture, the depth of sequence coverage was calculated as the number of reads containing a given target base averaged over the target area. It was observed that a significant and reproducible bias among the common target regions existed among the microarrays, such that coverage depth spanned nearly three orders of magnitude and was highly correlated between experiments (pairwise $0.85 < p < 0.99$).

Figure 4:
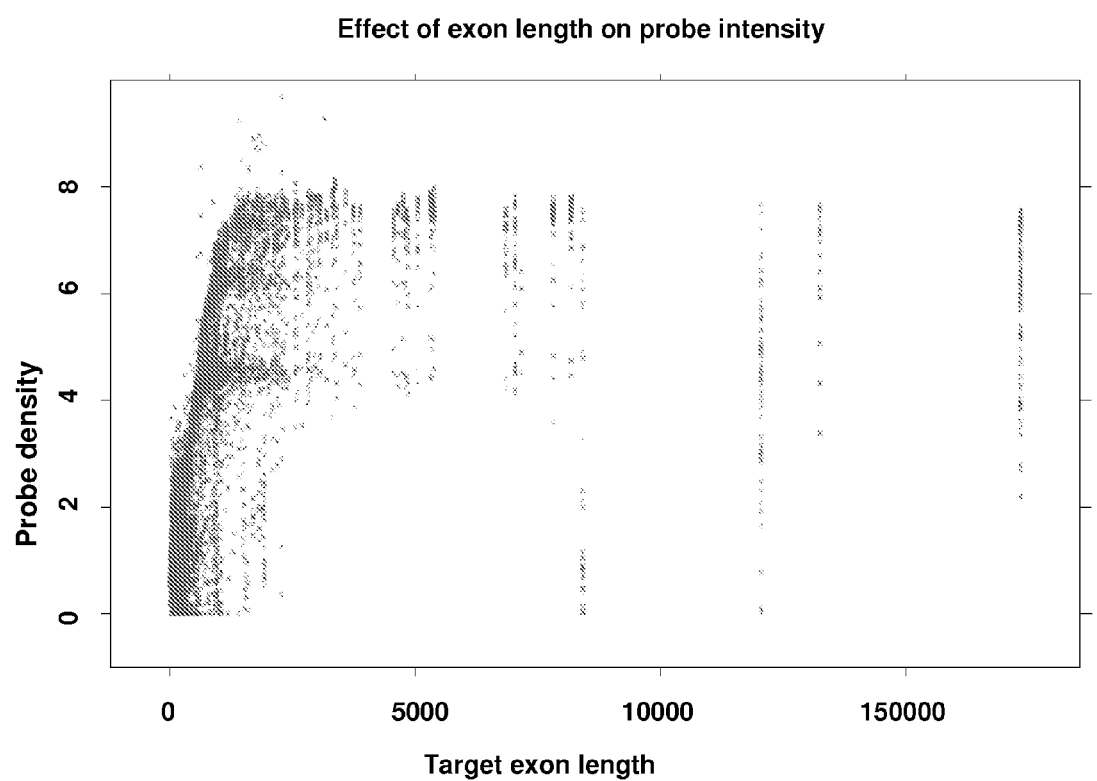
FIG. 4 demonstrates the effect of exon length on probe density.
Figure 5:
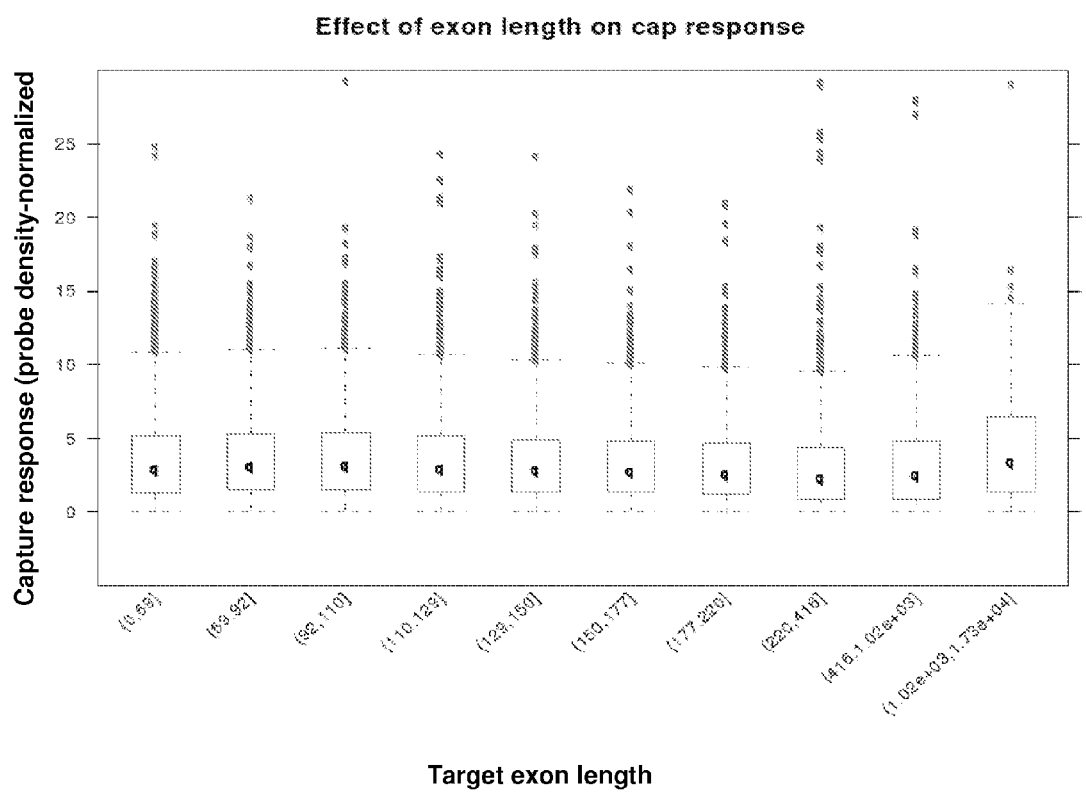
FIG. 5 demonstrates lack of any aggregate-level effect of exon length on probe capture response.

While performing experimentation in support of embodiments of the present invention, it was determined that exon length has an effect on probe density. FIG. 4 exemplifies experimentation performed utilizing a standard tiling microarray design. In a standard design, capture probes are typically disproportionally allocated to longer target intervals. The density of probes per target exon is greater for longer exons than shorter ones, thereby correlating a pattern of biased coverage toward longer target sequences. However, it was determined that probe capture response did not correlate with exon length. For example, FIG. 5 demonstrates sequence data from an experiment utilizing a standard microarray tiling design. The aggregate capture response distributions are shown within targets binned by length of the target exon. The distributions are not significantly different between shorter and longer target regions. The present invention is not limited to a particular mechanism. Indeed, an understanding of the mechanism is not necessary to practice the present invention. Nonetheless, it is contemplated that a lack of significant difference between shorter and longer target regions in capture response distribution indicates that a difference in coverage between the two groups of targets arises from non-uniform probe density.

The experimental arrays were designed to capture sequentially broader target regions, however each microarray comprised approximately the same total number of probes and the target regions common to all arrays were tiled at sequentially lower density. When comparing individual targets across the experiments, it was observed that each target's depth of sequencing was linearly dependent upon the local density of capture probes and the slope of this linear relationship in a particular target characterized to bias toward, or against, the capture of that target (FIG. 1c).

Based on observations, it was contemplated that redistribution of probe densities within a single array could be used to mitigate bias among targets. To that end, a generalized linear model of target relative abundance as a function of relative capture probe density was utilized after which constrained optimization was applied to distribute a fixed number of total capture probes to achieve a distribution of probes predicted to provide uniform coverage depth. This constrained optimization comprises a greedy algorithm to assign probes to regions in order to reach the desired distribution of target abundances. The algorithm takes several inputs: the fitted model, the desired final distribution of relative abundances over the targets, and the minimum and maximum probe densities allowable in any interval. The target read distribution is initially set to zero and is proportionally scaled in a stepwise fashion to reach the final desired distribution.

At each step, the probe count required to achieve the target read distribution is computed in each interval subject to the maximum and minimum probe density constraints. The algorithm terminates when the full count of available probes have been allocated. It is contemplated that any model relating target abundance to probe density is amendable to practicing the methods of the present invention in designing arrays with redistributed probes for uniform capture of target sequences. As such, the present invention provides methods and systems for probe redistribution, characterized in that the frequency of each individual sequence of the redistributed probes corresponds to the frequency of the corresponding target nucleic acid sequence with the population of target nucleic acid molecule sequences. Once the degree of capture response is determined for each oligonucleotide probe (e.g., based on the probe sequence and the calculations as defined herein), and the abundance of each nucleic acid probe, practicing the probe redistribution methods of the present invention, will therefore reciprocally correspond to the predetermined capture response of the target sequences (e.g., more target sequences, less probes for that region and vice versa).

Utilizing the model, the experimental arrays were designed to achieve unbiased capture and uniform depth of sequencing across an approximately 200 kb region shared among the arrays tested. For example, two capture arrays were synthesized; one being an array with approximately uniform probe density (FIG. 1d), and the second an array with redistributed probes (FIG. 1e). Sample DNA was hybridized to capture arrays, eluted, amplified, and sequenced. After aligning the reads from the experiments to the reference genome assembly coverage statistics were compared. Statistics revealed a significant increase in median coverage across the target regions (Table 1) after normalization of the variation in the total number of reads between the sequencing runs. When coverage depth was plotted across the target regions (FIG. 2), a significant improvement in uniformity of coverage among the target regions in the redistributed arrays was revealed. As such, it is demonstrated herein that methods of the present invention provide for capture arrays with a variety of coverage distributions, both uniform and intentionally non-uniform (e.g., to enrich exonic targets against intronic/intergenic target regions).

Figure 6:
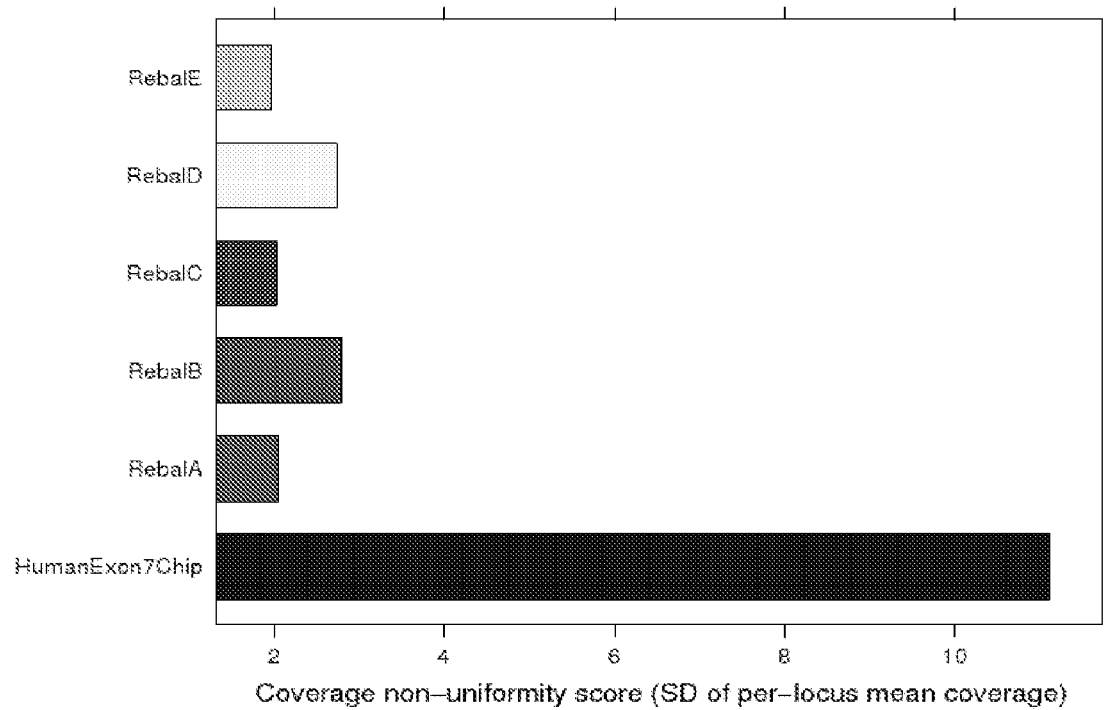
FIG. 6 depicts a comparison of the standard deviations of the target locus sequence coverage distributions from experiments using five different rebalanced designs (RebalA through RebalE) and a baseline (HumanExon7 Chip) following a standard tiling design.

The effect of practicing methods of the present invention for rebalancing probe distribution on a solid support for target sequence hybridization is further exemplified in FIG. 6. A comparison of standard deviations of target locus coverage distribution between five different rebalanced microarray designs (Rebal A through Rebal E) and a baseline microarray standard tiling design (HumanExon7 Chip) is shown. The data demonstrate a marked reduction in the non-uniformity score in the rebalanced arrays relative to baseline. A set of target loci common to all six designs was chosen and 140,000 reads were randomly sampled from the sequence data following capture with each design. Depth of coverage was calculated within each region and calculated data was plotted for each design as a cumulative distribution function indicating the percentage of target loci with coverage greater than or equal to a given level. Although an equal number of reads was selected from each capture, the baseline design has significantly more targets at aberrantly high coverage and consequently a high proportion of targets with zero coverage compared to the rebalanced designs (approximately 80% versus <20%).

Certain illustrative embodiments of the invention are described below. The present invention is not limited to these embodiments.

The present invention enables capturing and enriching for target nucleic acid molecules or target genomic region(s) from a complex biological sample by direct genomic selection. In some embodiments, the preferred embodiments find utility in searching for genetic variants and mutations, for example single nucleotide polymorphisms (SNP), or set of SNPs, that underlie human diseases. The elucidation of genetic variants and mutations allows for, for example, the study and characterization of diseases and other genetic disorders, including research into diagnosing and therapeutic treatments of diseases and disorders.

In some embodiments, the present invention provides a solid support, wherein the solid support comprises immobilized oligonucleotide probes and wherein said probes are distributed such that uniform, enriched capture of target nucleic acid molecules is realized. In some embodiments, the solid support is a microarray slide, whereas in other embodiments the solid support is a bead (e.g., in solution in a tube, in a well of a plate, etc.). In some embodiments, the solid support comprises a bead upon which is immobilized an oligonucleotide probe. The bead can be comprised of any variety of materials. For example, beads useful as solid supports in methods of the present invention may comprise, silica gel, glass, resin (e.g., Wang resin as found in U.S. Pat. No. 6,133,436; incorporated herein be reference in its entirety), metal plastic, cellulose, dextran (e.g., Sephadex®), agarose (e.g., Sepharose®), and the like. Beads are not limited by size, however beads in the range of about 1 to about 100 um is diameter are preferred.

Figure 3:
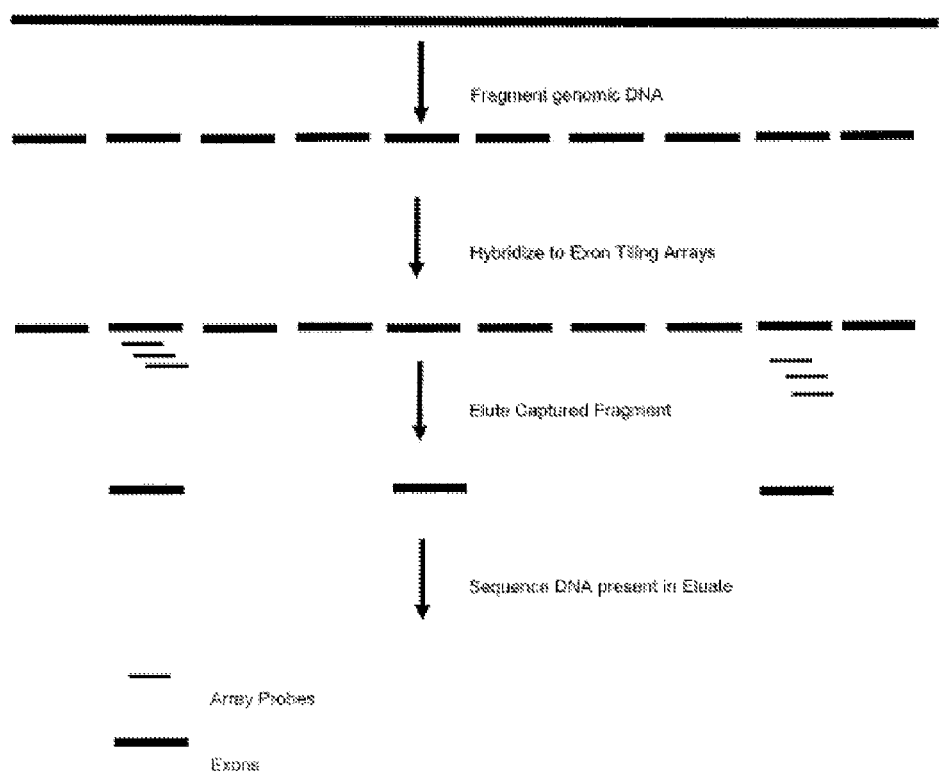
FIG. 3 demonstrates exemplary schematics for target enrichment: a) a schematic depicting nucleic acid molecules and probe utilization as found in an embodiment of the present invention, prior to probe redistribution, and b) a schematic of an exemplary microarray genomic target enrichment strategy of the present invention.
Figure 3:
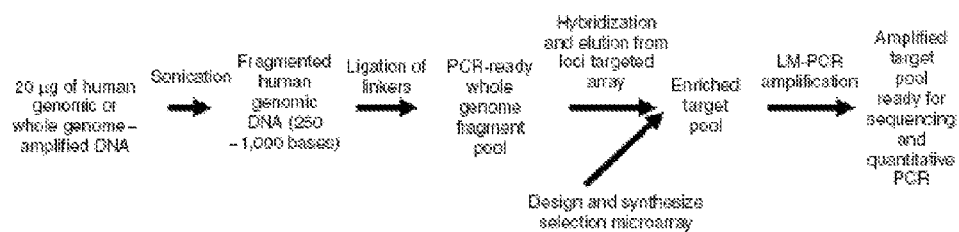

In some embodiments, the present invention comprises applying a sample of nucleic acid molecules, for example a sample of genomic DNA, to the solid support. In some embodiments, the sample is fragmented prior to applying to the solid support. In some embodiments, the fragmented nucleic acid molecules comprise linkers ligated to one or both of the fragment ends. In some embodiments, the fragments are denatured to create single stranded nucleic acids prior to applying said sample to the solid support. In some embodiments, the denatured, fragmented nucleic acid sample is applied to the solid support under conditions that allow for hybridization of target sequences in the nucleic acid sample to the oligonucleotide probe that comprise the associated target sequence. In some embodiments, the hybridized array is washed to remove unbound and non-specifically bound nucleic acid molecules. In some embodiments, the uniformly captured and enriched target sequences are eluted from the solid support and downstream applications performed on the eluted sequences (FIG. 3b).

In general, microarray oligonucleotides are designed to target a region or regions of a genome. In some embodiments, probes are designed to be overlapping probes, for example the starting nucleotides of adjacent probes are separated in the genome by less than the length of a probe, or non-overlapping probes, where the distance between adjacent probes are greater than the length of a probe. The overlapping of probes is oftentimes termed "tiling" of probes, thereby creating tiling arrays. In tiling arrays, the distance between adjacent probes is generally overlapping, with spacing between the starting nucleotide of two probes varying between, for example, 1 and 100 bases. It is contemplated that probes are tested for uniqueness in the genome. For example, to avoid non-specific binding of genomic elements to capture arrays, highly repetitive elements of the genome are excluded from selection microarray. The process compared the set of probes against a pre-computed frequency histogram of all possible 15-mer probes in the human genome. For each probe, the frequencies of the 15-mers comprising the probe are then used to calculate the average 15-mer frequency of the probe.

Immobilized probes correspond in sequence to one or more regions of the genome and are provided, in one embodiment, on a solid support in parallel using maskless array synthesis (MAS) technology as previously described. In some embodiments, probes are obtained serially using a standard DNA synthesizer and then applied to a solid support. In some embodiments, probes are obtained from an organism and immobilized on the solid support. In preferred embodiments the immobilized probes represent probe redistribution such that the probes provide for uniform capture of target sequences. In other embodiments, the immobilized probes represent probe redistribution that is non-uniform and defined as such by an investigator. Probe redistribution is determined by practicing the methods as described herein, for example as demonstrated in the Examples and figures herein. Fragmented nucleic acids are hybridized to the immobilized probes, and nucleic acids that do not hybridize, or that hybridize non-specifically to the probes are separated from the support-bound probes by washing. The remaining nucleic acids molecules that are specifically hybridized to the probes are eluted from the solid support (e.g., by heated water, by a nucleic acid elution buffer for example comprising TRIS buffer and/or EDTA) to yield an eluate enriched for uniformly captured target nucleic acid molecules.

In methods of the present invention, the nature and performance of the probes selected are varied to advantageously normalize and/or adjust the distribution of the target molecules captured and enriched. In some embodiments, probe normalization delivers one expressed gene per read. Normalization can be applied, for example, to populations of cDNA molecules before library construction, as the distribution of molecules in the population reflects the different expression levels of expressed genes from which the cDNA molecule populations are produced. For example, the number of sequencing reactions required to effectively analyze each target region can be reduced by normalizing the number of copies of each target sequence in the enriched population such that across the set of probes the capture performance of distinct probes is normalized, on the basis of a combination of fitness and other probe attributes. Fitness, characterized by a "capture metric," is ascertained either informatically or empirically. For example, the ability of the target molecules to bind is adjusted by providing so-called isothermal ($T_m$-balanced) oligonucleotide probes, as described in U.S. Published Patent Application Number 2005/0282209 (incorporated herein by reference in its entirety), that enable uniform probe performance, eliminate hybridization artifacts and/or bias and provide higher quality output. Probe lengths are adjusted (typically, about 20 to about 100 nucleotides, preferably about 40 to about 85 nucleotides, in particular about 45 to about 75 nucleotides, optionally more than 100 nucleotides until about 250 nucleotides) to equalize the melting temperature (e.g., $T_m$=76° C., typically about 55° C. to about 76° C., in particular about 72° C. to about 76° C.) across the entire set. In some embodiments, probes are optimized to perform equivalently at a given stringency in the genomic regions of interest, including AT- and GC-rich regions. In some embodiments, the sequence of individual probes is adjusted, using natural bases or synthetic base analogs such as inositol, or a combination thereof to achieve a desired capture fitness of those probes.

In some embodiments, locked nucleic acid probes, peptide nucleic acid probes and the like having structures that yield desired capture performance are employed. A skilled artisan will appreciate that probe length, melting temperature and sequence can be coordinately adjusted for any given probe to arrive at a desired capture performance for the probe. The melting temperature ($T_m$) of the probe can be calculated using, for example, the formula: $Tm=5\times(G_n+C_n)+1\times(A_n+T_n)$, where n is the number of each specific base (A, T, G or C) present on the probe.

In some embodiments, capture performance is normalized by ascertaining the capture fitness of probes in the probe set and adjusting the quantity of individual probes on the solid support accordingly. For example, if a first probe captures twenty times as much nucleic acid as a second probe, then the capture performance of both probes can be equalized by providing twenty times as many copies of the second probe, for example by increasing by twenty-fold the number of features displaying the second probe. If the probes are prepared serially and applied to the solid support, the concentration of individual probes in the pool can be varied in the same way. Still further, another strategy for normalizing capture of target nucleic acids is to subject the eluted target molecules to a second round of hybridization against the probes under less stringent conditions than were used for the first hybridization round. Apart from the substantial enrichment in the first hybridization that reduces complexity relative to the original genomic nucleic acid, the second hybridization is conducted under hybridization conditions that saturate all capture probes. It is contemplated that, as equal amounts of capture probes are provided on the solid support, saturation of the probes will ensure that substantially equal amounts of each target are eluted after the second hybridization and washing.

Another normalizing strategy follows the elution and amplification of captured target molecules from the solid support. Target molecules in the eluate are denatured using, for example, a chemical or thermal denaturing process, to a single-stranded state and are re-annealed. Kinetic considerations dictate that abundant species re-anneal before less abundant species. As such, by removing the initial fraction of re-annealed species, the remaining single-stranded species are balanced relative to the initial population in the eluate. The timing required for optimal removal of abundant species is determined empirically. The fragmented denatured nucleic acid molecules provided comprise an average size of about 100 to about 1000 nucleotide residues, preferably about 250 to about 800 nucleotide residues and most preferably about 400 to about 600 nucleotide residues (e.g., by nebulization of genomic DNA as found in European patent application EP 0 552 290; incorporated herein by reference in its entirety).

The parameters of genetic complexity reduction can be chosen almost arbitrarily, depending upon the user's desire for sequence selection, and are defined by the sequences of the oligonucleotide probes. In some embodiments, said probes define a plurality of exons, introns or regulatory sequences from a plurality of genetic loci.

In some embodiments, said probes define the complete sequence of at least one single genetic locus, said locus having a size of at least 100 kb and preferably at least 1 Mb or a size as specified above. In some embodiments, said probes define sites known to contain SNPs. In some embodiments, the probes define a tiling array. Such a tiling array in the context of the present invention is contemplated as being designed to capture the complete sequence of at least one complete chromosome in a uniform manner.

In some embodiments, the population of probes comprises at least a second probe for each target sequence that shall become enriched, characterized in that said second probe has a sequence which is complementary to said first sequence.

The solid support according to the present invention is either a nucleic acid microarray or a population of beads. Beads comprise, for example, glass, metal, ceramic or polymeric beads. If the solid support is a microarray, it is possible to synthesize the oligonucleotide capture probes in situ directly onto said solid support. For example, the probes may be synthesized on the microarray using a maskless array synthesizer (U.S. Pat. No. 6,375,903; incorporated herein by reference in its entirety). The lengths of the oligonucleotide probes may vary, are dependent on the experimental design and are limited only by the possibility to synthesize such probes. Preferably, the average length of the population of probes is about 20 to about 100 nucleotides, preferably about 40 to about 85 nucleotides, in particular about 45 to about 75 nucleotides. If the solid support is a population of beads, the capture probes are initially synthesized on a microarray using a maskless array synthesizer, then released or cleaved off according to known standard methods, optionally amplified and then immobilized on said population of beads according to methods known in the art. In some embodiments, the beads are packed into a column so that a sample is loaded and passed through the column for reducing genetic complexity. In some embodiments, hybridization takes place in an aqueous suspension comprising the beads with immobilized multiple oligonucleotide molecules.

In one embodiment, the oligonucleotide probes each carry a chemical group or linker, for example a moiety which allows for immobilization onto a solid support (e.g., an immobilizable group). For example, biotin is used for immobilization on a streptavidin coated solid support. In another embodiment, such a moiety is a hapten like digoxygenin, which is used for immobilization on a solid support coated with a hapten recognizing antibody (e.g. a digoxygenin binding antibody).

In some embodiments, nucleic acid probes for target nucleic acid molecules are synthesized on a solid support, released from the solid support as a pool of probes and amplified by, for example, PCR. In some embodiments, an amplified pool of released probes is covalently- or non-covalently immobilized onto a support, such as glass, metal, ceramic or polymeric beads or other solid support. In some embodiments, the probes are designed for convenient release from the solid support by providing, for example, at or near the support-proximal probe termini an acid- or alkali-labile nucleic acid sequence that releases the probes under conditions of low or high pH, respectively, or by incorporation in the probe termini a restriction endonuclease cleavage site, or other enzymatic cleavage, site. Various cleavable linker chemistries are known in the art. In some embodiments, the solid support is provided in a column having fluid inlet and outlet. In some embodiments, a biotinylated nucleotide is incorporated into the probe sequence and a support is coated with streptavidin for capture of a biotinylated probe.

The present invention comprises the capture of target nucleic acid sequences found in target nucleic acid molecules. Target nucleic acid molecules include nucleic acids from any source, in purified, substantially purified, or unpurified form. In some embodiments, the nucleic acid source material need not comprise a complete complement of genomic nucleic acid molecules from an organism. In some embodiments, the nucleic acid sample is biological. In some embodiments, the biological nucleic acid samples are obtained from animals and encompass nucleic acids isolated from fluids, solids, tissues, etc. In some embodiments, biological nucleic acid samples may also come from non-human animals, including, but are not limited to, vertebrates such as rodents, non-human primates, ovines, bovines, ruminants, lagomorphs, porcines, caprines, equines, canines, felines, aves, etc. In some embodiments, biological nucleic acids may also be obtained from plants, prokaryotes (e.g., bacteria) and viruses (e.g., DNA or RNA). However, it is contemplated that the present invention is not limited by the source of nucleic acids sample, and any nucleic acid from any biological Kingdom finds utility in methods as described herein. In preferred embodiments, nucleic acid samples are from humans, or derived from humans, for example from individual patients, tissue samples, or cell culture. As used herein, the term "target nucleic acid molecules" refers to molecules from a target genomic region to be studied. The pre-selected probes determine the range of targeted nucleic acid molecules. The skilled person in possession of this disclosure will appreciate the complete range of possible targets and associated targets.

Nucleic acid molecules of the present invention are typically deoxyribonucleic acids or ribonucleic acids, and include products synthesized in vitro by converting one nucleic acid molecule (e.g. DNA, RNA and cDNA) to another, as well as synthetic molecules containing nucleotide analogues. In preferred embodiments, the nucleic acid molecules are DNA molecules, preferably genomic DNA molecules. In some embodiments, the nucleic acid molecules are fragmented. In some embodiments, the nucleic acid molecules are denatured. In some embodiments, denatured DNA molecules, preferably genome derived molecules, are shorter than naturally occurring genomic nucleic acid molecules, comprising, for example, fragmented nucleic acid molecules.

A target sequence, or region, of the present invention comprises one or more continuous blocks of several megabases (Mb), or several smaller contiguous or discontiguous regions such as all of the exons from one or more chromosomes, or sites known to contain SNPs. For example, the solid support can support a tiling array designed to capture one or more complete chromosomes, parts of one or more chromosomes, all exons, all exons from one or more chromosomes, selected exons, introns and exons for one or more genes, gene regulatory regions, and so on. In some embodiments, to increase the likelihood that desired non-unique or difficult-to-capture targets are enriched, the probes can be directed to sequences associated with (e.g., on the same fragment as, but separate from) the actual target sequence, in which case genomic fragments containing both the desired target and associated sequences will be captured and enriched. The associated sequences can be adjacent or spaced apart from the target sequences, but the skilled person will appreciate that the closer the two portions are to one another, the more likely it will be that genomic fragments will contain both portions. In some embodiments, to further reduce the limited impact of cross-hybridization by off-target molecules, thereby enhancing the integrity of the enrichment, sequential rounds of capture using distinct but related capture probe sets directed to the target region is performed. Related probes are probes corresponding to regions in close proximity to one another in the genome that hybridize to the same genomic DNA fragment.

In some embodiments, uniform enrichment methods of the present invention comprise nucleic acid molecule fragments, for example genomic DNA fragments, in a size range compatible with the uniform post-enrichment technology in which the enriched fragments will be used. In some embodiments, fragment sizes comprise approximately 100 nucleotide to approximately 1000 nucleotide residues or base pairs, approximately 250 to approximately 800 nucleotide residues, approximately 400 to approximately 600 nucleotide residues, more preferably approximately 500 nucleotide residues or base pairs.

A skilled artisan can produce fragmented nucleic acid molecules of random- or non-random size from larger molecules by, for example, chemical, physical or enzymatic fragmentation or cleavage using well known protocols. Chemical fragmentation can employ, for example, ferrous metals (e.g., Fe-EDTA). Physical methods include, for example, sonication, hydrodynamic force or nebulization (e.g., European patent application EP 0 552 290; incorporated herein by reference in its entirety) and other shearing forces. Enzymatic protocols can employ, for example, nucleases such as micrococcal nuclease (Mnase) and exonuclease (such as ExoI or Bal31) or restriction endonucleases. The present invention is not limited by the method used to produce fragmented nucleic acid molecules, such as fragmented genomic DNA, indeed any fragmentation method is contemplated for use in providing fragmented nucleic acid molecules for practicing the present invention.

In some embodiments, the present invention provides methods for reducing genomic complexity and determining multiple sequences by incorporating the step of ligating adaptor molecules to one or both ends of fragmented nucleic acid molecules. In preferred embodiments, adaptors are ligated to both ends of fragmented nucleic acid molecules. In some embodiments, adaptor molecules of the present invention comprise blunt-ended double-stranded oligonucleotides. In some embodiments, the adaptors when ligated to the fragmented nucleic acid molecules provide sites for amplification of said nucleic acid molecules with at least one primer, said primer comprising a sequence which corresponds to or specifically hybridizes under hybridization conditions with the sequence of said adaptor molecules. In some embodiments, linkers range from approximately 12 to approximately 100 base pairs, from approximately 18 to approximately 80 base pairs, preferably from approximately 20 to approximately 24 base pairs.

When ligating blunt-ended primers to fragmented nucleic acids, it is contemplated that the fragmented nucleic acids are themselves blunt ended. Filling in the ends of nucleic acid molecules to create blunt ended molecules prior to ligation to other molecules, such as adaptor molecules, is well known in the art, for example by using methods comprising dNTPs and DNA polymerases such as T4-DNA polymerase or Klenow. The polished 5' ends of the fragmented nucleic acid molecules are then phosphorylated using, for example, T4 polynucleotide kinase which adds phosphate groups to the 5' termini allowing for subsequent ligation of the adaptor molecules. Ligation of the adaptor molecules is performed according to any method which is known in the art, for example by performing a ligase reaction comprising T4-DNA ligase.

In some embodiments, the ligation of adaptors to fragmented nucleic acid molecules in performed prior to hybridization to oligonucleotide probes, whereas in other embodiments it is performed after hybridization to oligonucleotide probes. It is preferential in embodiments where the ligation is performed subsequently, that the enriched nucleic acids which are released from the solid support in single stranded form are re-annealed followed by a primer extension reaction and a fill-in reaction according to standard methods known in the art.

In some embodiments, ligation of adaptor molecules allows for a step of subsequent amplification of the captured molecules. In some embodiments, the adaptor molecules comprise one sequence, resulting in a population of fragments with identical terminal sequences at both ends of the fragment. As such, it is sufficient to use only one primer in a potential subsequent amplification step. In some embodiments, adaptor molecules comprise two different sequences, for example sequence A and sequence B. As such, a population of enriched molecules composed of three different sequences at the ends of the fragmented nucleic acids can result; (i) fragments having one adaptor (A) at one end and another adaptor (B) at the other end, (ii) fragments having adaptors A at both ends, and (iii) fragments having adaptors B at both ends. Generation of enriched molecules according to type (i) is advantageous if amplification and sequencing is performed, for example, using the 454 Life Sciences Corporation GS20 and GSFLX instrument (GS20 Library Prep Manual, December 2006, PCT Patent Publication Number WO 2004/070007; incorporated herein by reference in their entireties).

In some embodiments, if one of said adaptors, for example adaptor B, comprises a biotin modification, then molecules (i) and (iii) can be captured on streptavidin (SA) coated magnetic particles for further isolation, and the products of (ii) washed away. In case the enriched and SA-immobilized DNA is single stranded following elution from the capture array/solid support, it is advantageous to make the DNA double-stranded. In this case primers complementary to adaptor A may be added to the washed SA pull down products. Since moieties that are B-B (iii above) do not have A or its complement available, only A-B adapted and SA captured products are made double stranded following primer-extension from an A complement primer. Subsequently, the double stranded DNA molecules bound to said magnetic particles are thermally or chemically (e.g. NaOH) denatured in such a way that the newly synthesized strand is released into solution. Due to the tight biotin/streptavidin bonding, molecules with two adaptors B will not be released into solution. The only strand available for release is the A-complement to B-complement primer-extension synthesized strand. Said solution comprising single stranded target molecules with an adaptor A at one end and an adaptor B at the other end can, for example, be subsequently bound on another type of bead comprising a capture sequence which is sufficiently complementary to the adaptor A or B sequences for further processing.

In some embodiments, the present invention is not limited to a particular set of hybridization conditions. However, stringent hybridization conditions as known to those skilled in the art, and as described herein, are preferably employed. In some embodiments, the present invention provides washing the hybridization reaction thereby removing unbound and non-specifically bound nucleic acid molecules. In some embodiments, the present invention provides washes of differential stringency, for example a wash buffer I comprising 0.2×SSC, 0.2% (v/v) SDS, and 0.1 mM DTT, a wash buffer II comprising 0.2×SSC and 0.1 mM DTT and a wash buffer III comprising 0.5×SSC and 0.1 mM DTT. The present invention is not limited by composition of the hybridization and/or wash buffers, indeed any composition is amenable in practicing methods of the present invention. In some embodiments, the hybridization target sequences are eluted from the solid support using, for example water or similar low solute solution known to those skilled in the art.

In some embodiments, the present invention provides uniform enrichment of target nucleic acid sequences for subsequent use in targeted array-based-, shotgun-, capillary-, or other sequencing methods known to the art. In general, strategies for shotgun sequencing of randomly generated fragments are cost-effective and readily integrated into a pipeline, but the invention enhances the efficiency of the shotgun approach by presenting uniformly enriched nucleic acid fragments from one or more genomic regions of interest for sequencing. As such, the present invention provides an ability to focus the sequencing strategies on specific genomic regions, such as individual chromosomes or exons (for example, by conscience non-uniform selection by non-uniform probe distribution) for, for example, medical sequencing purposes.

As known to a skilled artisan, sequencing by synthesis is understood to be a sequencing method which monitors the generation of side products upon incorporation of a specific deoxynucleoside-triphosphate during the sequencing reaction (Rhonaghi et al., 1998, Science 281:363-65; incorporated herein by reference in its entirety). For example, one or the more prominent embodiments of the sequencing by synthesis reaction is the pyrophosphate sequencing method. In pyrosequencing, generation of pyrophosphate during nucleotide incorporation is monitored by an enzymatic cascade which results in the generation of a chemo-luminescent signal. The 454 Genome Sequencer System (Roche Applied Science cat. No. 04760085001) is based on the pyrophosphate sequencing technology. For sequencing on a 454 GS20 or 454 FLX instrument, the average genomic DNA fragment size is preferably in the range of 200 or 600 bp, respectively. Sequencing by synthesis reactions can also comprise a terminator dye type sequencing reaction. In this case, the incorporated dNTP building blocks comprise a detectable label, such as a fluorescent label, that prevents further extension of the nascent DNA strand. The label is removed and detected upon incorporation of the dNTP building block into the template/primer extension hybrid, for example, by using a DNA polymerase comprising a 3'-5' exonuclease or proofreading activity.

In some embodiments, the uniformly enriched target sequences are eluted from the microarray and sequenced. In some embodiments, the sequencing is performed using a 454 Life Sciences Corporation sequencer. In some embodiments, the present invention provides target sequence amplification following elution by emulsion PCR (emPCR) following manufacturer's protocols. The beads comprising the clonally amplified target nucleic acids from the emPCR are transferred into a picoliter plate according to the manufacturer's protocol and subjected to a pyrophosphate sequencing reaction for sequence determination.

In some embodiments, data analysis is performed on the bound target sequences prior to, or instead of, elution. Data analysis if performed, for example, to determine the probe redistribution needed and to verify the probe redistribution once completed. Data analysis is performed using any array scanner, for example an Axon GenePix 4000B fluorescent scanner. Once data is captured by the scanner, bioinformatics programs are utilized to analyze the captured data. Bioinformatics programs useful in data analysis from fluorescent microarray formats include, but are not limited to Signal-Map™ (NimbleGen) and NimbleScan™ (NimbleGen) however any scanner and bioinformatics programs capable of capturing and analyzing data generated by the methods of the present invention are equally amenable. Data output can be read on, for example, any computer screen or other device capable of displaying data such as that found in FIG. 1.

In some embodiments, the present invention provides a kit comprising reagents and/or other components (e.g., buffers, instructions, solid surfaces, containers, software, etc.) sufficient for, necessary for, performing uniform enrichment (or non-uniform enrichment) of target nucleic acid molecules. Kits of the present invention are provided to a user in one or more containers (further comprising one or more tubes, packages, etc.) that may require differential storage, for example differential storage of kit components/reagents due to light, temperature, etc. requirements particular to each kit component/reagent. In some embodiments, a kit of the present invention comprises one or more double stranded adaptor molecules, whereas the adaptors comprise one or more sequences. In some embodiments, a kit comprises one or more solid supports, wherein said solid supports can be a microarray or a plurality of beads as disclosed here. In some embodiments, the kit of the present invention comprises at least one or more compounds and reagents for performing enzymatic reactions, for example one or more of a DNA polymerase, a T4 polynucleotide kinase, a T4 DNA ligase, an array hybridization solution, an array wash solution, and the like. In some embodiments, one or more wash solutions are provided in a kit, wherein said wash solutions comprise SSC, DTT and optionally SDS. In some embodiments, a kit of the present invention comprises one or more wash buffers, examples of which include, but are not limited to, Wash Buffer I (0.2×SSC, 0.2% (v/v) SDS, 0.1 mM DTT), and/or Wash Buffer II (0.2×SSC, 0.1 mM DTT) and/or Wash Buffer III (0.5×SSC, 0.1 mM DTT). In some embodiments, a kit comprises an array elution solution, wherein said elution solution comprises purified water and/or a solution containing TRIS buffer and/or EDTA. In some embodiments, a kit comprises a second adaptor molecule, wherein one oligonucleotide strand of said first or second adaptor molecule comprises a modification which allows for immobilization onto a solid support. For example, such a modification may be a biotin label which can be used for immobilization on a streptavidin coated solid support. Alternatively, such a modification may be a hapten like digoxygenin, which can be used for immobilization on a solid support coated with a hapten recognizing antibody.

The following examples are provided in order to demonstrate and further illustrate certain preferred embodiments and aspects of the present invention and are not to be construed as limiting the scope thereof.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

EXAMPLE 1

Initial Capture Array Design

Five sequence capture microarrays were designed that targeted nested regions of decreasing extents (5 Mbp, 2 Mbp, 1 Mbp, 500 Kbp, and 200 Kbp), each approximately centered on the coordinate chr17:38490539. A common database of probe sequences with median length 75 bp and capable of synthesis in no more than 188 cycles was created (Nimble-Gen, Madison Wis.). Each capture design was composed of no more than 385,000 probes selected from this database at the closest possible probe coordinate spacing within the respective genomic interval. Because the array capacity exceeded the number of unique probes in the targeted interval on the 200 Kbp and 500 Kbp designs, each probe was replicated eight and four times on those arrays, respectively.

EXAMPLE 2

Sample Preparation and Microarray Capture

Purified genomic DNA (Burkitt's lymphoma cell line, ATCC #NA04671) was purchased from the Coriell Institute for Medical Research (Coriell Cell Repositories, Camden N.J.) and amplified using a Qiagen Whole Genome Amplification Kit (Hilden, Germany). Following amplification, 20 μg of DNA was sonicated, yielding an average size of 500 bp fragments. The fragments were treated with the Klenow fragment of DNA polymerase I (New England Biolabs, Beverly Mass.) generating blunt-ends, and then 5' phosphorylated with polynucleotide kinase (New England Biolabs) following established protocols. Synthetic oligonucleotides linkers 5'-Pi-GAGGATCCAGAATTCTCGAGTT-3' (SEQ ID NO: 1) and 5'-CTCGAGAATTCTGGATCCTC-3' (SEQ ID NO: 2) were annealed and ligated to the ends of the fragmented genomic DNA. The linker adapted genomic DNA fragments were hybridized to capture microarrays in the presence of 1× NimbleGen hybridization buffer (NimbleGen) for approximately 65 hours at 42° C. with active mixing using a MAUI hybridization station (NimbleGen), following manufacturer's protocols. After hybridization, arrays were washed 3 times, 5 minutes each wash, with Stringent Wash Buffer (NimbleGen), following by rinsing with Wash Buffers 1, 2, and 3 (NimbleGen), following manufacturer's protocol for NimbleChip™ Arrays User's Guide for CGH Analysis. Captured DNA fragments were immediately eluted with 2×250 μl of water at 95° C. Samples were dried, resuspended, and amplified by ligation mediated polymerase chain reaction (LM-PCR) using primers complementary to the ligated linkers.

EXAMPLE 3

Sequencing and Sequence Data Processing

Linkers compatible with 454 sequencing (454, Branford CT) were ligated to the captured, eluted DNA fragments. The resulting fragments were amplified on beads using emulsion PCR (emPCR) and sequenced using the 454 sequencing instrument, following manufacturer's protocols. As each sequenced fragment contained the 20 bp linker for the LM-PCR, the majority of 454 sequencing reads comprised this linker sequence.

Standard quality filtering and base-calling functions of the 454 instrument were applied to yield sequence reads and corresponding quality scores. Adapter and sequencing primer sequences were removed from sequence reads. Prior to mapping reads to the human genome assembly hg18, repetitive portions of each read likely to map non-uniquely (e.g., align with high identity to multiple, disparate locations in the genome) were masked using WindowMasker (Morgulis et al., 2006, Bioinformatics 22:134-41; incorporated herein by reference in its entirety). Reads were mapped to the genome using NCBI MegaBLAST (Zhang et al., 2000, J Comput Biol 7:203-14; incorporated herein by reference in its entirety). After discarding matches to the genome demonstrating less than 95% identity, the remaining reads were classified as uniquely mapping if, for each read, there was either 1) only one match to the genome, or 2) a single best match could be clearly identified. In the latter case, a single match was selected from several if a single match had both the greatest length and strongest homology. Otherwise, the read was tagged as non-uniquely mapped. All subsequent analyses were restricted to uniquely-mapped reads.

EXAMPLE 4

Capture Data Analysis

Figure 1B:
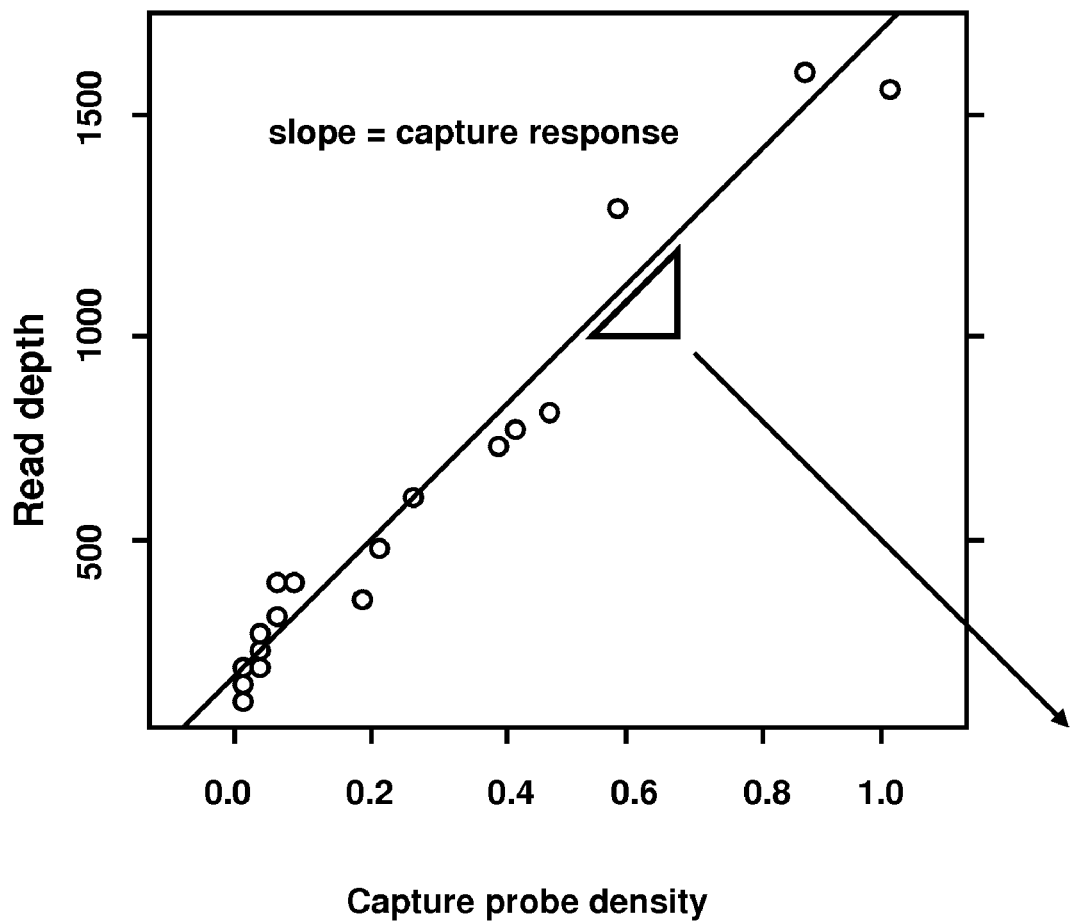
Figure 2:
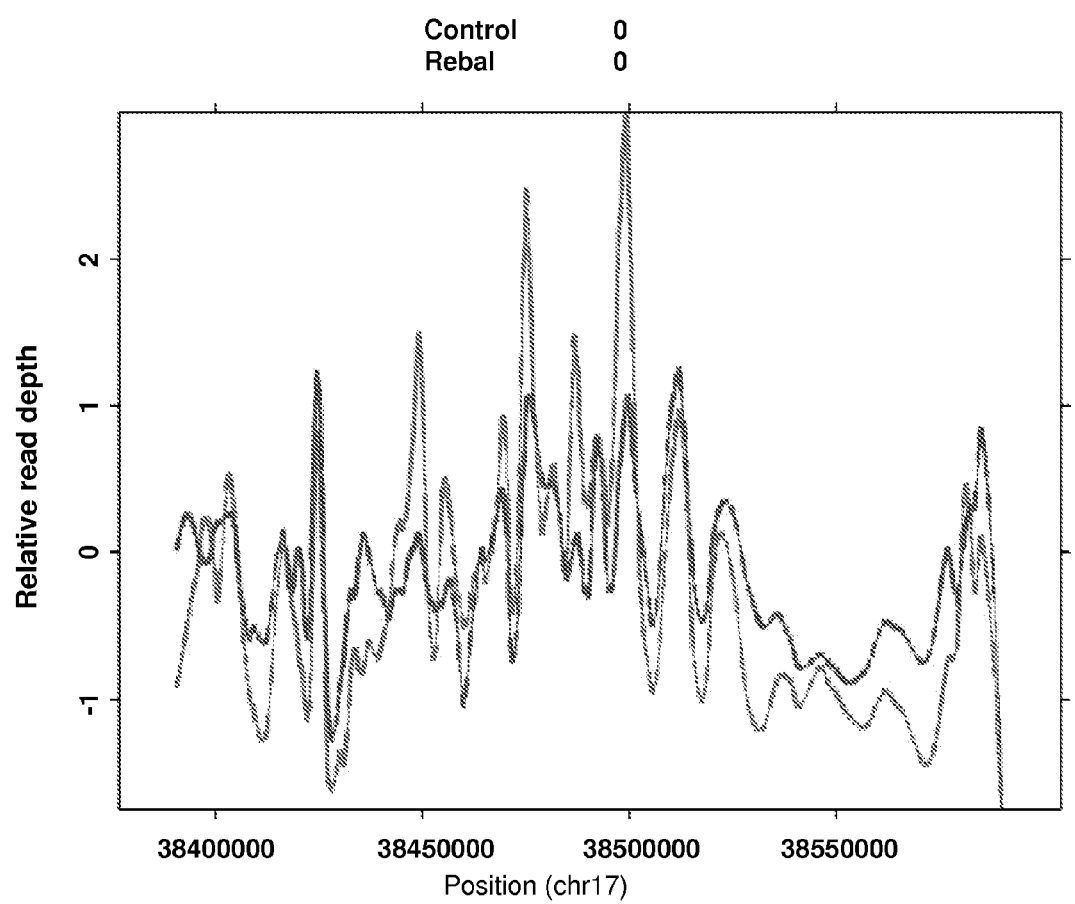
FIG. 2 demonstrates the relative coverage depth plotted along the capture target region of an exemplary control (Control, light line) and rebalanced (Rebal, dark line) probe redistribution experiment. The variance in coverage is less severe for the redistributed array when compared to the control array.

Capture probe density of a given genomic interval was calculated by averaging over each base in the interval the number of capture probes overlapping that base. Likewise, raw read depth at a given genomic interval was calculated by averaging over each base in the interval the number of uniquely-mapped sequencing reads overlapping that base. Read depths between separate capture/sequencing experiments were normalized by dividing by the cumulative number of sequenced bases uniquely mapped to the target regions. The central 200 kb interval covered by all five initial capture experiments was segmented into non-overlapping 100 bp windows and the read depth and capture probe density at each window were calculated (FIG. 1a). Within each window, linear regression was used to fit read depth to capture probe density, with the intercept constrained to (0,0); the resulting slope (or "capture response") in each window quantified the local capture affinity at that region (FIG. 1b).

EXAMPLE 5

Probe Redistribution

Capture probes in the initial five capture designs were placed approximately uniformly within the respective target interval (FIG. 1c). Likewise, a control design with uniform capture probe distribution across the central 200 Kbp target was prepared (FIG. 1d). An optimized design was prepared (FIG. 1e) by moving probes from regions of high capture response requiring fewer probes to regions needing more probes to meet the desired uniform read depth.

An empirically-fit, linear regression model from the initial set of capture experiments was used to predict the read depth resulting from a given density of capture probes at each targeted region, thereby allowing for the best distribution of target probes to optimally produce uniform read depth following capture and sequencing.

Table 1 demonstrates exemplary sequence coverage statistics for control and redistributed capture arrays. After correcting the data for experimental variation following sequence capture (e.g., median coverage divided by the number of target reads), the redistributed array demonstrates an approximately 20% improvement in capture uniformity over the control array (last column).

TABLE 1

|  | Control | Redistributed |
|---|---|---|
| Total reads | 342796 | 383658 |
| Total bps | 7.15E+07 | 7.52E+07 |
| Total matches | 465564 | 532545 |
| Below 95% threshold | 27.14% (126333) | 33.22% (176928) |
| No match | 24.93% (85453) | 38.82% (148950) |
| Mapped uniquely | 73.60% (252284) | 59.60% (228658) |
| Bps mapped uniquely | 78.13% (55873369) | 65.39% (49201425) |
| Target bases covered | 146295 | 151732 |
| % Target bases covered | 95.00% | 98.50% |
| # Reads in target region | 16.11% (40649) | 32.76% (74905) |
| Ave coverage | 57.3 | 102.8 |
| Median coverage | 42 | 93 |
| Capture uniformity | 100.00% | 120.16% |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method for uniform enrichment of a population of nucleic acid molecules in a sample, comprising:
   a) providing a sample of nucleic acid molecules comprising a plurality of target nucleic acid sequences,
   b) hybridizing the sample to nucleic acid probes complementary to the target nucleic acid sequences under hybridization conditions, wherein at least one of the target nucleic acid sequences exhibits enrichment bias for a complementary probe, and wherein the frequency of individual nucleic acid probe sequences is increased for a target nucleic acid sequence having below-average enrichment and decreased for a target nucleic acid sequence having above-average enrichment such that the nucleic acid probes provide uniform hybridization among said plurality of target nucleic acid sequences, and
   c) separating non-hybridized nucleic acid sequences from hybridized target nucleic acid sequences, thereby uniformly enriching a population of nucleic acid molecules in a sample.

2. The method of claim 1, wherein said separating comprises washing said support.

3. The method of claim 1, further comprising fragmenting said sample of nucleic acid molecules prior to said hybridizing.

4. The method of claim 3, further comprising ligating an adaptor molecule to one or both ends of a plurality of fragmented nucleic acid molecules prior to said hybridizing.

5. The method of claim 4, further comprising denaturing said sample of nucleic acid molecules prior to said hybridizing.

6. The method of claim 1, further comprising eluting a plurality of hybridized target nucleic acid sequences from the support.

7. The method of claim 6, further comprising sequencing the eluted target nucleic acid sequences.

8. The method of claim 1, wherein said nucleic acid probes are immobilized on a support.

9. The method of claim 8, wherein said support is a microarray slide or a bead.

10. The method of claim 1, wherein said population of nucleic acid molecules is a population of genomic DNA molecules.

11. The method of claim 1, wherein said population of nucleic acid molecules is a population of amplified genomic DNA molecules.

12. The method of claim 1, wherein the frequency is determined by utilizing an empirically-fit linear regression model.

13. A process for uniform enrichment of a population of nucleic acid sequences in a sample, said process comprising hybridizing a plurality of immobilized hybridization probes to a plurality of corresponding target nucleic acid sequences within a population of nucleic acid molecules and separating non-hybridized nucleic acid sequences from hybridized target nucleic acid sequences, wherein at least one of the target nucleic acid sequences exhibits enrichment bias for a complementary probe, and wherein the frequency of individual hybridization probes is increased for target nucleic acid sequences having below-average enrichment and decreased for target nucleic acid sequences having above-average enrichment such that the nucleic acid probes provide uniform hybridization among said plurality of target nucleic acid sequences.

14. The process of claim 13, further comprising eluting said hybridized target nucleic acid sequences.

15. The process of claim 13, wherein the immobilized hybridization probes are immobilized on a microarray slide or a bead.

16. The process of claim 15, wherein the frequency is determined utilizing an empirically-fit linear regression model.

17. The process of claim 13, wherein said target nucleic acid sequences are genomic DNA sequences.

18. A method for uniform enrichment of a population of nucleic acid molecules in a sample, comprising:
   a) providing a sample of nucleic acid molecules comprising a plurality of target nucleic acid sequences,
   b) hybridizing the sample to a support comprising immobilized nucleic acid probes under conditions to support hybridization between the immobilized nucleic acid probes and the plurality of target nucleic acid sequences, wherein said immobilized nucleic acid probes are complementary to said plurality of target nucleic acid sequences, wherein the density of said immobilized nucleic acid probes to optimally produce uniform read depth is predicted using an empirically-fit, linear regression model fitting read depth to the density of immobilized nucleic acid probes, and wherein the immobilized nucleic acid probes provide uniform hybridization among said plurality of target nucleic acid sequences, and
   c) separating non-hybridized nucleic acid sequences from hybridized target nucleic acid sequences, thereby uniformly enriching a population of nucleic acid molecules in a sample.

19. The method of claim 18, wherein said separating comprises washing said support.

20. The method of claim 18, further comprising fragmenting said sample of nucleic acid molecules prior to said hybridizing.

21. The method of claim 20, further comprising ligating an adaptor molecule to one or both ends of a plurality of fragmented nucleic acid molecules prior to said hybridizing.

22. The method of claim 21, further comprising denaturing said sample of nucleic acid molecules prior to said hybridizing.

23. The method of claim 18, further comprising eluting a plurality of hybridized target nucleic acid sequences from the support.

24. The method of claim 23, further comprising sequencing the eluted target nucleic acid sequences.

25. The method of claim 18, wherein said support is selected from the group consisting of a microarray slide and a bead.

26. The method of claim 18, wherein said population of nucleic acid molecules is a population of genomic DNA molecules.

27. The method of claim 18, wherein said population of nucleic acid molecules is a population of amplified genomic DNA molecules.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: DNA oligonucleotide

<400> SEQUENCE: 1
gaggatccag aattctcgag tt                                              22

```
<210> SEQ ID NO 2
<211> LENGTH: 20
<212> TYPE: DNA
<213> ORGANISM: Artificial Sequence
<220> FEATURE:
<223> OTHER INFORMATION: DNA oligonucleotide

<400> SEQUENCE: 2
ctcgagaatt ctggatcctc                                              20
```